United States Patent
Schwarz et al.

(10) Patent No.: US 6,569,844 B1
(45) Date of Patent: *May 27, 2003

(54) PHARMACEUTICAL PREPARATIONS CONTAINING ESTRA-1,3,5(10)-TRIENE DERIVATIVES

(75) Inventors: Sigfrid Schwarz, Jena; Walter Elger, Berlin; Hans-Joachim Siemann, deceased, late of Jena, by Christel Siemann, heir; Margit Lucas, heir, Mettmann; Frank Siemann, heir, Mitweida; Gudrun Reddersen; Birgitt Schneider, both of Jena, all of (DE)

(73) Assignee: Jenapharm GmbH & Co., KG, Jena (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/750,930

(22) PCT Filed: Jul. 3, 1995

(86) PCT No.: PCT/DE95/00879

§ 371 (c)(1),
(2), (4) Date: Feb. 2, 1998

(87) PCT Pub. No.: WO96/05217

PCT Pub. Date: Feb. 22, 1996

(30) Foreign Application Priority Data

Aug. 9, 1994 (DE) .......................................... 44 29 398

(51) Int. Cl.[7] ......................... A61K 31/56; A61K 31/58
(52) U.S. Cl. ..................... 514/176; 514/178; 514/179; 514/182; 514/841; 514/842; 514/843
(58) Field of Search ................................ 514/176, 182, 514/178, 179

(56) References Cited

U.S. PATENT DOCUMENTS 5,286,737 A * 2/1994 Kato et al. .................. 514/383

FOREIGN PATENT DOCUMENTS

| DE | 1949095 | * | 9/1970 |
| DE | 114806 | * | 8/1975 |
| DE | 207447 | * | 2/1984 |
| WO | 93/05064 | * | 3/1993 |

OTHER PUBLICATIONS

Doctoral Thesis; Title: Erythrocytes As A Drug Carrier—Investigations With Selected Estrogens For Loading Following Oral Administration; Author: Dr. Claus Claussen; Date: Aug., 1989; Research Institute: Natural Science Faculty, Science Council, Martin–Luther University Halle–Wittenberg.

Doctoral Thesis; Title: Animal Experimental Contribution To The Development Of Estrogenic Substances; Author: Wolfgang Stölzner; Date: Jul. 18, 1989; Research Institute: Mathematisch–Naturwissenschaftlich–Technischen faculty of Friedrich–Schiller–University Jena.

* cited by examiner

*Primary Examiner*—Barbara P. Badio
(74) *Attorney, Agent, or Firm*—Wood, Phillips, VanSanten, Clark & Mortimer

(57) ABSTRACT

The invention concerns pharmaceutical preparations containing estra-1,3,5(10)-triene derivatives as active ingredients which carry a group of the general formula

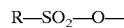

at their C3 position wherein R is a $R^1R^2N$ group wherein $R^1$ and $R^2$ are independent of each other and represent a hydrogen atom, a $C_1$–$C_5$ alkyl radical or, together with the N atom, a polymethylene imino radical containing 4 to 6 C atoms, or a morpholino radical.

The preparations according to the invention can be used for hormonal contraception and for hormon replacement therapy (HRT). They exhibit a low hepatic estrogenity.

4 Claims, No Drawings

PHARMACEUTICAL PREPARATIONS CONTAINING ESTRA-1,3,5(10)-TRIENE DERIVATIVES

This application is a 371 of PCT/DE95/00879 filed Jul. 3, 1995.

DESCRIPTION

This invention relates to pharmaceutical preparations containing active ingredients that are estra-1,3,5(10)-triene derivatives having an R—$SO_2$—O group at their C3 position.

Estrogens play a major role in hormonal contraception, in menopausal hormone replacement therapy (HRT), and for treating gynecologic (e.g. mammary carcinoma) and andrologic (e.g. prostatic carcinoma) diseases.

For HRT and contraception, estrogens are mainly used together with a gestagen, e.g. levornogestrel, desogestrel, gestodene, drospirorenone, norethisterone, cyproterone acetate, chlormadinone acetate, dienogest.

When used for contraception, estrogens are needed for safely suppressing follicle maturation and ovulation, but in addition they replace the endogenous ovarian secretion of estradiol which is suppressed to a major extent. This replacement is important for maintaining an artificial menstrual cycle and other genital functions, which could not be done to any satisfactory extent by just using a gestagen.

Moreover, endogenous estrogens have important central nervous and metavolic functions in female organism.

Normal estrogen levels contribute very much to a person's well-being (L. Zichella; Clinical Management of the Menopausal Woman; Int. J. of Fertil. and Menop. Studies, 38, Suppl. 1 (1993), pp. 15–22). Estrogens antagonize the development of cardiovascular diseases through various mechanisms, that is, by creating "favourable" lipoprotein patterns in the blood (G. Samsioe; Hormone Replacement and Cardiovascular Disease; Int. J. of Fertil. and Menop. Studies, 39, Suppl. 1 (1993), pp. 23–29), by inhibiting lipid deposits in the vessel wall (B. Clarkson; Experimental Effects of Progesterone versus Progestins on Arterial Wall; Gynecol. Endocrinol., 6, Suppl. 1 (1992), p. 15), by exerting a favourable influence on vascular tonus, thus reducing blood pressure (R. A. Lobo; Estrogen and Cardiovascular Disease; Ann. New York Acad. Sciences, 592 (1990), pp. 286–294), by reducing resistance to perfusion in important vessel sections and sedating contractile stimuli to the vascular muscle (C. Jiang et al.; Acute effect of 17β-estradiol on rabbit coronary artery contractile responses to endothelin-1; Am. J. Physiol., 263 (1992), H271–H275). The interior walls of vessels release factors (prostacyclin) under the influence of estrogens that counteract the development of blood clots.

Estrogens are indispensable for preserving the bone structure in women. If they are gone, this may cause destruction of the bone (osteoporosis) (C. Christiansen; Prevention and Treatment of Osteoprosis with Hormone Replacement Therapy; Int. J. of Fertil. and Menop. Studies, 38, Suppl. 1 (1993), pp. 45–54). These latter "central nervous" and "metabolic" effects of estrogens are a main aspect of HRT.

But notwithstanding all positive aspects of estrogen therapy there are unsolved problems, too, which restrict the therapeutic use of estrogens or entail undesired effects.

Natural estrogens (estradiol, estrone, estrone sulfate, esters of estradiol, estriol) become bioavailable only to a very low degree when taken orally (K. B. Lokind et al.; Oral bioavailability of 17β-estradiol and various ester prodrugs in the rat; Int. J. Pharmaceutics, 76 (1991), pp. 177–182). This degree may vary so much from person to person that general dosage recommendations cannot be given. These pharmacokinetic factors resulted in a negative evaluation of natural estrogens for contraception (W. Kuhnz et al.; Pharmacokinetics of Estradiol, Free and Total Estrone, in Young Women Following Single Intravenous and Oral Administration of 17β-Estradiol; Arzneimittel-Forschung/Drug Res., 43 (II), 9, (1993), pp. 966–973). Fast elimination of the substances from the blood is another problem. Estrogen replacement under HRT often has to be adjusted to the individual. Development of an estradiol prodrug designed to improve bioavailability therefore proved to be unsuccessful (K. B. Lokind et al.; see above).

Synthetic estrogens also have considerable disadvantages. The most important synthetically altered estrogenic steroid is ethinyl estradiol (EE). This estrogen is dominant in oral contraception. Apart from EE, mestranol is used in a few cases; this is a "prodrug" that is metabolized to EE in the organism (J. W. Goldzieher; Selected aspects of the pharmacokinetics and metabolism of ethinyl estrogens and their clinical implications; Am. J. Obstet. Gynecol., 163 (1990), pp. 318–322). When applied orally to humans, EE has a much better bioavailability than the natural estrogens mentioned above, but its oral bioavailability varies to an extraordinary extent from individual to individual. Goldzieher pointed out the negative meaning, from a pharmacodynamic point of view, of the variation of the area under the curve (AUC), of half-life and the time at which maximum concentrations in the blood are reached. The highest AUC found in this study, measured 0 to 24 hours after application, was 2121 pg×h/ml. The lowest AUC was 284 pg×h/ml. A similar variation of the AUC around a factor of 6 or 7 was described in Hümpel et al. (M. Hümpel et al.; Comparison of Serum Ethinyl Estradiol, Sex-Hormone-Binding Globulin, Corticoid-Binding Globulin and Cortisol Levels in Women Using Two Low-Dose Combined Oral Contraceptives; Horm. Res., 33 (1990), pp. 35–39).

After resorption from the intestinal lumen, orally applied active ingredients enter the organism via the liver. This fact is of specific importance for estrogenic agents as the liver is a target organ for estrogens; oral intake of estrogens results in strong estrogenic effects in the liver. The secretion activity that is controlled by estrogens in the human liver includes synthesis of transport proteins CBG, SHBG, TBG, angiotensinogen, several factors that are important for the physiology of blood clotting, and lipoproteins.

If natural estrogens are introduced to the female organism while avoiding passage through the liver (e.g. by transdermal application), the liver functions mentioned remain virtually unchanged (U. Larsson-Cohn et al.; Some biochemical consequences of post-menopausal hormone replacement treatment; in: The Controversial Climacteric, Ed.: P. A. van Keep et al.; MTP Press Ltd. (1982)). Therapeutically equivalent doses of natural estrogens, when applied orally, result in clear responses of hepatic parameters: increase of SHBG, CBG, angiotensinogen, HDL (high density lipoprotein) (J. C. Stevenson et al.; Oral Versus Transdermal Hormone Replacement Therapy; Int. J. of Fertil. and Menop. Studies, 38, Suppl. 1 (1993), pp. 30–35). These hepatic effects of estrogen are clearly stronger when, instead of natural estrogens, equine estrogen formulations (so-called conjugated estrogens) are used (C. A. Mashchak et al.; Comparison of pharmacodynamic properties of various estrogen formulations; Am. J. Obstet. Gynecol., 144 (1982) pp. 511–518). Ethinyl estradiol and DES have an even greater hepatic estrogenicity. When referring to antigonadotropic properties, EE is about 8 to 10 times more estrogenic in the liver than orally applied natural estrogens are. This is a very unfavourable dissociation of properties (B. von Schoultz et al.; Estrogen Therapy and Liver Function—Metabolic Effects of Oral and Parenteral Administration; The Prostate, 14, (1989), pp. 389–395).

The following observation shows that undesired hepatic responses to estrogen cannot be avoided by lowering EE doses in contraceptives. A reduction from 30 µg to 20 µg of EE, each time combined with 150 µg of the same gestagen, showed no reduction of the considerably increased angiotensin level after three months, and just marginally reduced values after 6 months (A. Basdevant et al.; Hemostatic and metabolic effects of lowering the ethinyl estradiol dose from 30 mcg to 20 mcg in oral contraceptives containing desogestrel; Contraception, 48 (1993), pp. 193–204).

A known complication that may occur after applying high doses of estrogen to males suffering from prostatic carcinoma is fatal thromboembolism (B. von Schoultz et al.; see above).

The potential of EE to produce side effects in the liver determines, though in a somewhat weakened form, the strategy of oral hormonal contraception.

In view of desired contraceptive effects and maintenance of the menstrual process on the one hand, and the need to take into account the considerable side effect potential on the other, controlling EE levels in the blood may be compared to a tightrope walk. It is quite possible that a large percentage of women cannot apply oral contraceptives because either menstrual bleeding abnormities or estrogen-related side effects exceed the tolerance threshold.

Hormonal contraceptives increase the risk of suffering from, and dying of, certain cardiovascular diseases significantly (V. Wynn; Oral contraceptives and coronary disease; J. Reprod. Med., 36, Suppl. 3, (1991), pp. 219–225). As such risks are age-dependent (J. I. Mann; Oral contraceptives and myocardial infarction in young women; Pharmacol. steroid. Contracept. Drugs, Editors S. Garrattini and H. W. Berendes, Raven Press, New York, (1977), pp. 289–296), several health authorities have warned not to apply hormonal contraceptives to women older than 35 years. Women over 35 years of age who are smokers and use hormonal contraceptives are exposed to striking cardiovascular risks (F. A. Leidenberger; Klinische Endokrinologie für Frauenärzte, pp. 382–383; J. I. Mann; see above). The risk of fatal cardiovascular diseases is increased by a factor of 5 to 6 in women using oral contraceptives compared with control populations (F. A. Leiden-berger; see above). These findings prove that oral contraceptives cannot be used at all, or only at an unjustifiably high risk, by large groups of fertile women.

According to the state of the art, this problem is to be attributed to the estrogen component in hormonal contraceptives and not to the gestagen component (Skouby et al.; J. Obstet. Gynekol.; (1990), 1535–1537). A "consensus meeting" found that the risk of fatal myocardial infarctions is independent of the application period. This finding proves that the formation of clots that cause death does not take place in the heart due to defects of the arterial wall (atherosclerosis) but in the liver due to acute effects on hemostatic functions (R. A. Lobo, see above). A reduction of estrogenic effects in the liver therefore appears to be an appropriate way to eliminate the risks of hormonal contraception and the application restrictions mentioned. The risks described for EE are expressly excluded for natural estrogens, i.e. estrogens that have a lower hepatic estrogenicity compared with EE (R. A. Lobo; see above).

HRT based on natural hormones generally requires individual dose adjustment when today's techniques are used. Such treatment poses many imponderabilities; there is a clear risk of over- or underdosing.

It is therefore a problem of the present invention to provide pharmaceutical preparations that do not show the disadvantageous effects and side effects described.

This problem is solved according to the invention by providing pharmaceutical preparations containing estra-1,3,5(10)-triene derivatives as active ingredients that carry a group of the general formula

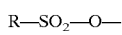

at their C3 position wherein
R is a $R^1R^2N$ group
wherein $R^1$ and $R^2$ are independent of each other and represent a hydrogen atom, a $C_1$–$C_5$ alkyl radical or, together with the N atom, a polymethylene imino radical containing 4 to 6 C atoms, or a morpholino radical.

The estra-1,3,5(10)-triene derivatives contained in the pharmaceutical preparations according to the invention, and carrying an R—SO$_2$—O group at their C3 position, and in which R has the meaning specified above, may optionally contain further double bonds between C atoms 6 and 7, 7 and 8, 8 and 9, 9 and 11, 8 and 14, 14 and 15, and/or 15 and 16.

The estra-1,3,5(10)-triene derivatives contained in the pharmaceutical preparations according to the invention, and carrying an R—SO$_2$—O group at their C3 position, and in which R has the meaning specified above, may optionally carry oxo-groups at C atoms 6, 7, 11, 15, 16 and/or 17.

The estra-1,3,5(10)-triene derivatives contained in the pharmaceutical preparations according to the invention, and carrying an R—SO$_2$—O group at their C3 position, and in which R has the meaning specified above, may carry additional hydroxy groups, optionally esterified or etherified, at C atoms 6, 7, 9, 11, 14, 16 and/or 17. The hydroxy groups are esterified using common derivatives of physiologically acceptable anorganic and organic acids, for example, phosphoric acid, sulfuric acid, oxalic acid, maleic acid, fumaric acid, lactic acid, tartaric acid, malic acid, citric acid, salicylic acid, valeric acid, adipic acid, and benzoic acid. Other acids that can be used are described, for example, in Fortschritte der Arzneimittelforschung, vol. 10, pp. 224–225, Birkhäuser Verlag, Basel and Stuttgart, 1966, and Journal of Pharmaceutical Sciences, vol. 66, pp. 1–5 (1977). The hydroxy groups are etherified using common derivatives of aliphatic alcohols containing up to 6 carbon atoms.

The estra-1,3,5(10)-triene derivatives contained in the pharmaceutical preparations according to the invention, and carrying an R—SO$_2$—O group at their C3 position, and in which R has the meaning specified above, may, at C atoms 6, 7, 11, 14, 15, 16 and/or 17, optionally carry additional alkyl residues, alkylidene residues, alkenyl residues, and alkynyl residues containing up to 5 carbon atoms, said residues optionally themselves carryingsimilar residues or a halogen.

The estra-1,3,5(10)-triene derivatives contained in the pharmaceutical preparations according to the invention, and carrying an R—SO$_2$—O group at their C3 position, and in which R has the meaning specified above, may optionally carry additional alkylene or alkenylene residues containing up to 3 carbon atoms between C atoms 14 and 15 or 14 and 17.

Among the 3-Sulfamate-estra-1,3-5(10)-triene derivatives contained, according to the invention, in pharmaceutical preparations, and carrying an R—SO₂—O group at their C3 position, and in which R has the meaning specified above, may be, for example, 17β-hydroxy-estra-1,3,5(10)-trien-3-yl sulfamate,
17β-hydroxy-estra-1,3,5(10)-trien-3-yl N,N-diethyl-sulfamate,
17β-hydroxy-estra-1,3,5(10)-trien-3-yl N,N-dimethyl-sulfamate,
17β-hydroxy-estra-1,3,5(10),7-tetraen-3-yl N,N-diethyl-sulfamate,
17β-hydroxy-estra-1,3,5(10),6,8-pentaen-3-yl N,N-dimethyl-sulfamate,
17-oxo-estra-1,3,5(10)-trien-3-yl sulfamate,
17-oxo-estra-1,3,5(10)-trien-3-yl N,N-dimethyl-sulfamate,
17-oxo-estra-1,3,5(10)-trien-3-yl N,N-diethyl-sulfamate,
16α,17β-dihydroxy-estra-1,3,5(10)-trien-3-yl sulfamate,
16α,17β-dihydroxy-estra-1,3,5(10)-trien-3-yl N,N-dimethyl-sulfamate,
16α,17β-dihydroxy-estra-1,3,5(10)-trien-3-yl N,N-diethyl-sulfamate,
2,17β-dihydroxy-estra-1,3,5(10)-trien-3-yl N,N-dimethyl-sulfamate,
2-methoxy-17β-hydroxy-estra-1,3,5(10)-trien-3-yl N,N-diethyl-sulfamate,
17β-hydroxy-19-nor-17α-pregna-1,3,5(10)-trien-20-in-3-yl sulfamate,
17β-hydroxy-19-nor-17α-pregna-1,3,5(10)-trien-20-in-3-yl N-methyl-sulfamate,
17β-hydroxy-19-nor-17α-pregna-1,3,5(10)-trien-20-in-3-yl N,N-dimethyl-sulfamate,
17β-hydroxy-19-nor-17α-pregna-1,3,5(10)-trien-20-in-3-yl N,N-diethyl sulfamate
17β-hydroxy-19-nor-17α-pregna-1,3,5(10)-trien-20-in-3-yl pyrrolidinosulfonate,
17β-hydroxy-14α,15α-methylene-estra-1,3,5(10)-trien-3-yl N,N-dimethyl-sulfamate,
17β-hydroxy-14α,15α-methylene-estra-1,3,5(10)-trien-3-yl N,N-diethyl-sulfamate,
17β-hydroxy-14α,15α-methylene-estra-1,3,5(10)-trien-3-yl pyrrolidinosulfonate,
17β-hydroxy-14α,15α-methylene-estra-1,3,5(10)-trien-3-yl morpholinosulfonate,
17β-hydroxy-14α,15α-methylene-estra-1,3,5(10)-trien-3-yl N-methyl-sulfamate,
17β-hydroxy-14α,15α-methylene-estra-1,3,5(10)-trien-3-yl sulfamate,
17β-hydroxy-14α,15α-methylene-estra-1,3,5(10)-7-tetraen-3-yl N,N-dimethyl-sulfamate,
17β-hydroxy-14α,15α-methylene-estra-1,3,5(10)-6,8-pentaen-3-yl N,N-diethyl-sulfamate,
17β-hydroxy-14α,15α-methylene-estra-1,3,5(10)-8-tetraen-3-yl N,N-dimethyl-sulfamate,
11β-chloromethyl-17β-hydroxy-estra-1,3,5(10)-trien-3-yl N, N-dimethyl sulfamate,
17β-hydroxy-14α,17α-vinylene-estra-1,3,5(10)-trien-3-yl N, N-diethyl-sulfamate,
14α,17α-ethylene-17β-hydroxy-estra-1,3,5(10)-trien-3-yl pyrrolidinosulfonate,
16α,17β-dihydroxy-14α,17α-ethylene-estra-1,3,5(10)-trien-3 yl N,N-diethyl-sulfamate,
17β-hydroxy-7α-methyl-estra-1,3,5(10)-trien-3, 11β-diyl 3-N, N-dimethyl-sulfamate-11-nitrate and
17β-hydroxy-11β-methoxy-19-nor-17α-pregna-1,3,5 (10)-trien-20-in-3-yl N,N-dimethyl-sulfamate.

Preferred pharmaceutical preparations according to the invention contain estra-1,3,5(10)-triene derivatives of the general formula I

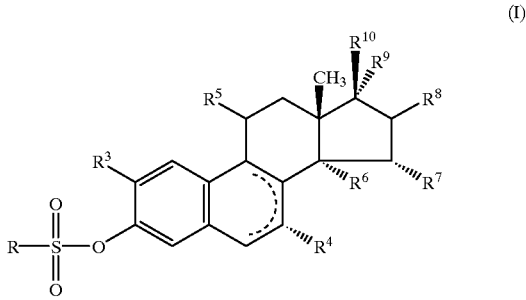

(I)

wherein
R is a R¹R²N group
wherein R¹ and R² are independent of each other and represent a hydrogen atom, a C₁–C₅ alkyl radical or, together with the N atom, a polymethylene imino radical having 4 to 6 C atoms, or a morpholino residue,
R³ is a hydrogen atom, a hydroxy group, or an alkoxy group containing 1 to 5 C atoms,
R⁴ is a hydrogen atom or a C₁–C₅ alkyl radical,
R⁵ is a hydrogen atom, a hydroxy group, an esterified hydroxy group, a haloalkyl or alkoxy group containing 1 to 5 C atoms,
R⁶ and R⁷ are hydrogen atoms, or together form a methylene group,
R⁸, R⁹ and R¹⁰ are independent of each other and represent a hydrogen atom or a hydroxy group,
with ring B optionally containing one or two double bonds or, optionally,
R⁹ being an alkynyl radical containing up to 5 carbon atoms or
R⁹ and R¹⁰ together forming an oxygen atom or
R⁶ and R⁹ representing a vinylene or ethylene group.

Particularly preferred are pharmaceutical preparations according to the invention that contain estra-1,3,5(10)-triene derivatives of the general formula I, and where R⁵ and R⁶ represent hydroxy groups.

Furthermore, particularly preferred pharmaceutical preparations according to the invention contain estra-1,3,5(10)-triene derivatives of the general formula I where R³ and R⁴ together represent a methylene group.

Much preferred are pharmaceutical preparations containing

17β-hydroxy-19-nor-17α-pregna-1,3,5(10)-trien-20-in-3-yl N, N-diethyl sulfamate
17β-hydroxy-19-nor-17α-pregna-1,3,5(10)-trien-20-in-3-yl pyrrolidinosulfonate,
17β-hydroxy-estra-1,3,5(10)-trien-3-yl N,N-diethyl-sulfamate,
17β-hydroxy-14α,15α-methylene-estra-1,3,5(10)-trien-3-yl N, N-diethyl-sulfamate, 16α,17β-dihydroxy-estra-1,3,5(10)-trien-3-yl N,N-dimethyl-silfamate, estra-1,3,5(10)-trien-17-on-3-yl N,N-diethyl-sulfamate, 17β-hydroxy-19-nor-17α-pregna-1,3,5(10)-trien-20-in-3-yl N, N-dimethyl sulfamate, 17β-hydroxy-14α,15α-methylen-estra-1,3,5(10)-trien-3-yl N, N-dimethyl-sulfamate, and 16α,17β-dihydroxy-estra-1,3,5(10)-trien-3-yl N,N-diethyl-sulfamate.

The estra-1,3,5(10)-triene derivatives contained in the pharmaceutical preparations according to the invention are produced in a generally known way by reacting an estra-1,3,5(10)-triene derivative with an accordingly substituted amidosulfonyl chloride, thereby esterifying the 3-OH group of the estra-1,3,5(10)-triene derivative.

The reaction is carried out in the usual way using a 2-phase system in the presence of a quaternary ammonium salt as a phase transition catalyst. Reaction temperatures are in the range from room temperature to 100° C. The solvents used are typical 2-phase systems such as chloroform-water, dichloro-methane-water, toluene-water, etc.

Some of the compounds contained in the preparations according to the invention are known.

Thus WO93/05064 describes the use of estrone-3-sulfamates as steroid sulfatase inhibitors.

DD 207 447 describes the use of N,N-dialkyl sulfamate derivatives of ethinyl estradiol as an agent to fight rodents.

Moreover, DE-OS 2426779, DE-OS 2426778, and DE-OS 2426777 describe 3-sulfamate derivatives of estratrienes that carry an additional hydroxyl group at their position 1.

In addition, DD 77 709 and DD 114 806 describe the preparation of the active ingredients contained in the pharmaceutical preparations according to the invention.

As yet, however, no pharmaceutical preparations are known that contain 3-sulfamates of estra-1,3,5(110)-triene derivatives as active ingredients and can be used for contraception, HRT, and carcinoma treatment.

Another object of this invention is the use of estra-1,3,5(10)-triene derivatives that carry a group of the general formula

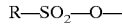
R—SO$_2$—O— at their C3 position wherein

R is a R$^1$R$^2$N group
wherein R$^1$ and R$^2$ are independent of each other and represent a hydrogen atom, a C$_1$–C$_5$ alkyl radical or, together with the N atom, a polymethylene imino radical containing 4 to 6 C atoms, or a morpholino radical, in the production of pharmaceuticals for hormonal contraception, climacteric hormone replacement therapy, and treatment of gynecologic and andrologic diseases such as mammary and prostatic carcinomas.

Preferred for producing pharmaceuticals for hormonal contraception, climacteric hormone replacement therapy, and treatment of gynecologic and andrologic diseases such as mammary and prostatic carcinomas, are estra-1,3,5(10)-triene derivatives of the general formula I

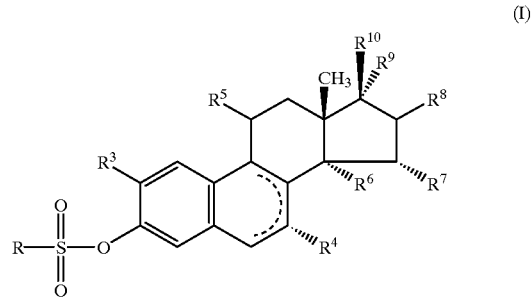

(I)

wherein

R is a R$^1$R$^2$N group
wherein R$^1$ and R$^2$ are independent of each other and represent a hydrogen atom, a C$_1$–C$_5$ alkyl radical or, together with the N atom, a polymethylene imino radical having 4 to 6 C atoms, or a morpholino radical, R$^3$ is a hydrogen atom, a hydroxy group, or an alkoxy group containing 1 to 5 C atoms, R$^4$ is a hydrogen atom or a C$_1$–C$_5$ alkyl radical, R$^5$ is a hydrogen atom, a hydroxy group, an esterified hydroxy group, a haloalkyl or alkoxy group containing 1 to 5 C atoms, R$^6$ and R$^7$ are hydrogen atoms, or together form a methylene group, R$^8$, R$^9$ and R$^{10}$ are independent of each other and represent a hydrogen atom or a hydroxy group, with ring B optionally containing one or two double bonds or, optionally, R$^9$ being an alkynyl radical containing up to 5 carbon atoms or R$^9$ and R$^{10}$ together forming an oxygen atom or R$^6$ and R$^9$ representing a vinylene or ethylene group.

For example,

17β-hydroxy-estra-1,3,5(10)-trien-3-yl sulfamate,

17β-hydroxy-estra-1,3,5(10)-trien-3-yl N,N-diethyl-sulfamate,

17β-hydroxy-estra-1,3,5(10)-trien-3-yl N,N-dimethyl-sulfamate,

17β-hydroxy-estra-1,3,5(10),7-tetraen-3-yl N,N-diethyl-sulfamate,

17β-hydroxy-estra-1,3,5(10),6,8-pentaen-3-yl N,N-dimethyl-sulfamate, 17-oxo-estra-1,3,5(10)-trien-3-yl sulfamate, 17-oxo-estra-1,3,5(10)-trien-3-yl N,N-dimethyl-sulfamate, 17-oxo-estra-1,3,5(10)-trien-3-yl N,N-diethyl-sulfamate, 16α,17β-dihydroxy-estra-1,3,5(10)-trien-3-yl sulfamate, 16α,17β-dihydroxy-estra-1,3,5(10)-trien-3-yl N,N-dimethyl-sulfamate, 16α,17β-dihydroxy-estra-1,3,5(10)-trien-3-yl N,N-diethyl-sulfamate, 2,17β-dihydroxy-estra-1,3,5(10)-trien-3-yl N,N-dimethyl-sulfamate, 2-methoxy-17β-hydroxy-estra-1,3,5(10)-trien-3-yl N,N-diethyl-sulfamate, 17β-hydroxy-19-nor-17α-pregna-1,3,5(10)-trien-20-in-3-yl sulfamate, 17β-hydroxy-19-nor-17α-pregna-1,3,5(10)-trien-20-in-3-yl N-methyl sulfamate 17β-hydroxy-19-nor-17α-pregna-1,3,5(10)-trien-20-in-3-yl N, N-dimethyl-sulfamate,
17β-hydroxy-19-nor-17α-pregna-1,3,5(10)-trien-20-in-3-yl N, N-diethyl-sulfamate
17β-hydroxy-19-nor-17α-pregna-1,3,5(10)-trien-20-in-3-yl pyrrolidinosulfonate,
17β-hydroxy-14α,15α-methylene-estra-1,3,5(10)-trien-3-yl N, N-dimechyl-sulfamate,
17β-hydroxy-14α,15α-methylen-estra-1,3,5(10)-trien-3-yl N, N-diethyl-sulfamate,
17β-hydroxy-14α,15α-methylen-estra-1,3,5(10)-trien-3-yl pyrrolidinosulfonate,
17β-hydroxy-14α,15α-methylen-estra-1,3,5(10)-trien-3-yl morpholinosulfonate,
17β-hydroxy-14α,15α-methylen-estra-1,3,5(10)-trien-3-yl N-methyl-sulfamate,
17β-hydroxy-14α,15α-methylen-estra-1,3,5(10)-trien-3-yl sulfamate,
17β-hydroxy-14α,15α-methylen-estra-1,3,5(10)-7-tetraen-3-yl N,N-dimethyl-sulfamate,
17β-hydroxy-14α,15α-methylen-estra-1,3,5(10)-6,8-pentaen-3-yl N,N-diethyl-sulfamate,
17β-hydroxy-14(15α-methylen-estra-1,3,5(10)-8-tetraen-3-yl N,N-dimethyl-sulfamate,
11β-chloromethyl-17β-hydroxy-estra-1,3,5(10)-trien-3-yl N, N-dimethyl sulfamate,
17β-hydroxy-14α,17α-vinylen-estra-1,3,5(10)-trien-3-yl N, N-diethyl-sulfamate,
14α,17α-ethylene-17β-hydroxy-estra-1,3,5(10)-trien-3-yl pyrrolidinosulfonate,
16α,17β-dihydroxy-14α,17α-ethylen-estra-1,3,5(10)-trien-3-yl N,N-diethyl-sulfamate,
17β-hydroxy-17α-methyl-estra-1,3,5(10)-trien-3,1ll-diyl 3-N, N-dimethyl-sulfamate-11-nitrate and
17β-hydroxy-11β-methoxy-19-nor-17α-pregna-1,3,5 (10)-trien-20-in-3-yl N,N-dimethyl-sulfamate are used for producing pharmaceuticals according to the invention for hormonal contraception, climacteric hormone replacement therapy, and treatment of gynecologic and andrologic diseases such as mammary and prostatic carcinomas.

The pharmaceutical preparations according to the invention contain, in addition, one or several of the gestagens mentioned above, such as levonorgestrel, desogestrel, gestodene, drospirorenone, norethisterone, cyproterone acetate, chlormadinone acetate, dienogest.

Furthermore, the pharmaceutical preparations according to the invention may be in the form of multi-step or compound preparations.

A compound preparation according to the invention may be composed, for example, of a first step containing a combination of several components, i.e. a natural estrogen, a synthetic estrogen, a progestin and/or an estra-1,3,5(10)-triene derivative, each carrying an R—SO$_2$—O group at its C3 position wherein R has the meaning specified above, and, optionally, one or several further steps containing either a pharmaceutically safe placebo or a natural or synthetic progestin or a biogenous or synthetic estrogen or an estra-1,3,5(10)-triene derivative, each carrying an R—SO$_2$—O group at its C3 position wherein R has the meaning specified above, or a combination of several components, i.e. a biogenous estrogen, a synthetic estrogen, a gestagen, an estra-1,3,5(10)-triene derivative, each carrying an R—SO$_2$—O group at its C3 position wherein R has the meaning specified above, or a combination of synthetic estrogens or an estra-1,3,5(10)-triene derivative, each carrying an R—SO$_2$—O group at its C3 position wherein R has the meaning specified above, and a gestagen.

The biogenous estrogen comprises, for example, an ingredient of the estradiol, estrone, estrane, estriol group and other biogenous estrogens, or at least a compound that splits off one of the estrogen ingredients mentioned soon after intake.

The synthetic estrogen comprises, according to the invention, at least one ingredient of the ethinyl estradiol, mestranol group and other synthetic estrogens, or at least one compound that splits off one of the estrogen ingredients mentioned soon after intake.

The gestagen comprises, according to the invention, at least one ingredient of the levonorgestrel, desogestrel, dienogest, progesterone, norethisterone acetate, chlormadinone acetate, gestodene, cyproterone acetate and other natural and/or synthetic gestagens, or at least one compound that splits off one of the gestagen ingredients mentioned soon after intake.

Another object of this invention is to provide pharmaceutical preparations that can be used for hormonal contraception, climacteric hormone replacement therapy, and treatment of gynecologic and andrologic diseases such as mammary and prostatic carcinomas.

Another object of this invention are pharmaceutical preparations in the form of tablets, tablets with controlled release, lozenges, pills, capsules, film tablets, and film tablets with controlled release.

The pharmaceuticals of the invention are produced in a known way using the usual solid or liquid substrates or diluents and the common adjuvants used in pharmaceutical engineering and with an appropriate dosage depending on the intended mode of application. Preferred formulations are those forms suitable for oral administration, for example, tablets, film tablets, lozenges, capsules, pills, powder, solutions, suspensions, or depot forms.

Tablets may be obtained, for example, by intermixing the active substance with known adjuvants, for example, inert diluents such as dextrose, sugar, sorbitol, mannite, polyvinylpyrrolidone, blasting agents such as maize starch or alginic acid, binders such as starch or gelatin, lubricants such as magnesium stearate or talcum and/or materials by which to produce a depot effect, such as carboxyl polymethylene, carboxymethyl cellulose, cellulose acetate phthalate or polyvinyl acetate. Tablets may consist of several layers.

Lozenges may be produced accordingly by coating cores manufactured in analogy to tablet manufacture using agents generally applied to lozenge coating, for example, polyvinylpyrrolidone or shellac, Arabic gum, talcum, titanium dioxide, or sugar. The coating of the lozenge may also consist of several layers in which the adjuvants mentioned in the paragraph on tablets can be used.

Capsules containing active ingredients may be produced, for example, by mixing the active substance with an inert substrate such as lactose or sorbitol, and encapsulating such mixture in gelatin capsules.

Because of the serious disadvantages of conventional estrogen derivatives used in medicine, there is, however, an urgent need for appropriate pharmaceutical preparations that are free of said disadvantages.

Despite the fact that some of the active ingredients of the pharmaceutical preparations according to the invention have been known for quite some time and have been well examined by pharmacologists, their favourable properties with regard to hepatic functions have not yet been described.

It was found, surprisingly, that the active agents used according to the invention do better than EE as regards estrogenic efficiency but, while showing maximum estrogenic effects in the uterus, are not more estrogenic in the liver than the natural estrogen estradiol. This combination of therapeutic properties is a decisive improvement of the active agents of the invention as compared with natural or synthetic estrogens. Contraceptives according to the invention containing estra-1,3,5(10)-triene derivatives carrying an R—SO$_2$—O group at its C3 position wherein R has the meaning specified above, require a completely new definition of application restrictions in hormonal contraception as they have little or no effect on the hemostatic system.

Contraceptives according to the invention containing estra-1,3,5(10)-triene derivatives carrying an R—SO$_2$—O group at its C3 position wherein R has the meaning specified above can be given at such high doses due to dramatically reduced estrogenic effects that control of the menstrual cycle is also improved as compared to conventional EE derivatives.

Application of ethinyl estradiol (EE) in hormone replacement therapy is strictly rejected at present because of possible side effects. When using estra-1,3,5(10)-triene derivatives of the invention carrying an R—SO$_2$—O group at its C3 position wherein R has the meaning specified above, risks that exist for non-natural (biogenous) estrogens are eliminated. If compared with natural estrogens that are dominant in hormone replacement therapy today, targetability is much improved as oral bioavailability is defined and does not vary from person to person as with biogenous estrogens.

Hepatic estrogenicity was proved in ovariectomated rats. The laboratory animals, adult female rats (breeder: HSD/WIN:WU) were ovariectomated on day 14. Treatment started two weeks later by a single oral application per day of the respective test substance. The dosages given for esters refer to the steroid portion of the substances. Experimental groups and numbers of laboratory animals are given in Table 1. The tests were made in three groups (A, B, C) at various points in time. This is why there is a deviation in control group values. The tests of series A, B, and C can therefore be compared among each other if the values for the respective control groups are taken into account.

TABLE 1

Survey of tests made, substances tested, animal numbers, and dosages

| | Experiment A | | | | | Experiment B | | Experiment C | |
|---|---|---|---|---|---|---|---|---|---|
| | Dosage (µg/animal/day/p.o. d1–d7) | | | | | | | | |
| Substances | 0 | 0.1 | 1 | 10 | 100 | 0 | 10 | 0 | 10 |
| Control | 16 | | | | | 14 | | 8 | |
| E2 (1) | | 6 | 6 | 6 | 6 | | 8 | | |
| EE (1) | | 6 | 6 | 6 | 6 | | 8 | | |
| J 824 (1) | | 6 | 6 | 6 | 6 | | 8 | | |
| J 271 (B 2) | | 6 | 6 | 6 | 6 | | 8 | | |

TABLE 1-continued

Survey of tests made, substances tested, animal numbers, and dosages

| | Experiment A | | | | | Experiment B | | Experiment C | |
|---|---|---|---|---|---|---|---|---|---|
| | Dosage (µg/animal/day/p.o. d1–d7) | | | | | | | | |
| Substances | 0 | 0.1 | 1 | 10 | 100 | 0 | 10 | 0 | 10 |
| J 981 (B 4) | | | | | | | 8 | | |
| J 272 (B 3) | | | | | | | 8 | | |
| J 665 (B 8) | | | | | | | 8 | | |
| J 982 (B 9) | | | | | | | 8 | | |
| J 983 (B 5) | | | | | | | 8 | | |
| J 893 (1) | | | | | | | 8 | | |
| E1 (1) | | | | | | | 8 | | |
| J 804 (B 7) | | | | | | | 8 | | |
| E3 (1) | | | | | | | | | 8 |
| J 984 (B 6)? | | | | | | | | | 7 |
| J 989 (B 6)? | | | | | | | | | 8 |

(1) reference substances
(B X) Substances used according to the invention, X giving the number of the example
E2 (estradiol), EE (ethinyl estradiol), E1 (estrone)
E3 (estratriol)

The procedure of allocating animals to groups was randomized. The experiment was carried out as a block test. The animals were weighed at the beginning and at the end of the experiment.

The start of treatment was defined as day 1 (=d1), treatment was finished on day 7 (=d7); the animals were killed on day 8, various organs (uteri, adrenal glands, liver) were removed, weighed and deep-frozen (−196° C.) for further examination.

Blood was taken from the retrobulbar plexus under ether anaesthesia prior to treatment (d0), and on (d4) and (d8). IGF$_1$, angiotensin I, cholesterol and HDL cholesterol were determined in the serum obtained.

Methods of determination:

IGF$_1$: RIA by bioMérieux Co.;

angiotensin: modified RIA for renin activity by Sorin Co. cholesterol/HDL: enzymatic tests, photometric determination, reagents by Dr Bruno Lange GmbH.

The results of the experiment are given in Tables 2 to 7 below:

Effects on uterus growth (see Table 2)

The effect of the compound according to Example 2 has reached a plateau at an oral dose of 0.01 mg/animal/day. There is clear superiority to EE and great superiority to estradiol.

TABLE 2

Oral estrogenic effects:
Influence on sexual function
Uterus weights (mg, mean value ± standard deviation) as a function of dosage

| | Experiment A | | | | | Experiment B | | Experiment C | |
|---|---|---|---|---|---|---|---|---|---|
| | Dosage (µg/animal/day/p.o. d1–d7) | | | | | | | | |
| Substances | 0 | 0.1 | 1 | 10 | 100 | 0 | 10 | 0 | 10 |
| Control | 149.07 ± 17.52 | | | | | 164.08 ± 13.5 | | 185.4 ± 27.0 | |
| E2 | | 123.3 ± 21.2 | 128.9 ± 9.8 | 130.7 ± 11.7 | 285.4 ± 68.2 | | 182.3 ± 16.78 | | |

TABLE 2-continued

Oral estrogenic effects:
Influence on sexual function
Uterus weights (mg, mean value ± standard deviation) as a function of dosage

| | Experiment A | | | | | Experiment B | | Experiment C | |
|---|---|---|---|---|---|---|---|---|---|
| | Dosage (μg/animal/day/p.o. d1–d7) | | | | | | | | |
| Substances | 0 | 0.1 | 1 | 10 | 100 | 0 | 10 | 0 | 10 |
| EE | | 152.2 ± 20.8 | 195.8 ± 31.1 | 282.4 ± 42.2 | 441.2 ± 46.3 | | 352.59 ± 37.54 | | |
| J 824 | | 147.9 ± 14.4 | 220.1 ± 48.4 | 435.3 ± 76.9 | 559.1 ± 83.6 | | 537.5 ± 102.7 | | |
| J 271 | | 144.2 ± 19.6 | 289.9 ± 22.3 | 605.1 ± 118.5 | 563.6 ± 44.3 | | 540.8 ± 56.1 | | |
| J 981 | | | | | | | 225.34 ± 37.3 | | |
| J 272 | | | | | | | 620.7 ± 104.3 | | |
| J 665 | | | | | | | 639.48 ± 82.83 | | |
| J 982 | | | | | | | 193.4 ± 20.1 | | |
| J 983 | | | | | | | 348.6 ± 78.8 | | |
| J 893 | | | | | | | 524.5 ± 65.8 | | |
| E1 | | | | | | | 170.63 ± 22.8 | | |
| J 804 | | | | | | | 166.0 ± 22.5 | | |
| E3 | | | | | | | | | 301.94 ± 58.5 |
| J 984 | | | | | | | | | 245.63 ± 57.0 |
| J 989 | | | | | | | | | 182.79 ± 20.5 |

TABLE 3

Oral estrogenic effects:
Influence on the function of the adrenal glands
Weights of adrenal glands (mg, mean value ± standard deviation) as a function of dosage

| | Experiment A | | | | | Experiment B | | Experiment C | |
|---|---|---|---|---|---|---|---|---|---|
| | Dosage (μg/animal/day/p.o. d1–d7) | | | | | | | | |
| Substances | 0 | 0.1 | 1 | 10 | 100 | 0 | 10 | 0 | 10 |
| Control | 59.99 ± 8.8 | | | | | 53.0 ± 3.9 | | 53.1 ± 4.2 | |
| E2 | | 49.3 ± 4.3 | 57.9 ± 6.52 | 61.6 ± 7.8 | 54.4 ± 9.1 | | 54.4 ± 2.7 | | |
| EE | | 53.7 ± 8.6 | 58.9 ± 8.0 | 59.0 ± 5.8 | 80.8 ± 7.3 | | 56.6 ± 6.6 | | |
| J 824 | | 54.5 ± 8.4 | 56.7 ± 6.7 | 74.8 ± 12.2 | 76.1 ± 9.7 | | 63.7 ± 7.3 | | |
| J 271 | | 57.1 ± 7.6 | 57.4 ± 7.9 | 63.1 ± 6.3 | 66.5 ± 8.9 | | 57.9 ± 6.0 | | |
| J 981 | | | | | | | 50.5 ± 3.9 | | |
| J 272 | | | | | | | 57.5 ± 8.2 | | |
| J 665 | | | | | | | 58.0 ± 7.8 | | |
| J 982 | | | | | | | 55.3 ± 5.8 | | |
| J 983 | | | | | | | 53.9 ± 4.0 | | |
| J 893 | | | | | | | 53.5 ± 6.3 | | |
| E1 | | | | | | | 49.8 ± 6.3 | | |
| J 804 | | | | | | | 53.9 ± 8.1 | | |
| E3 | | | | | | | | | 52.2 ± 8.4 |
| J 984 | | | | | | | | | 59.3 ± 7.6 |
| J 989 | | | | | | | | | 52.8 ± 6.4 |

Effects on adrenal gland weights (see Table 3) Gains in adrenal gland weight are observed depending on dosage. Exception: Estradiol, clearly lower increase rate as compared to EE.

Effects on $IGF_1$ (see Table 4) All substances tested reduce IGFa in the course of the experiment at a dose of 100 μg/animal. Exception: Estradiol

TABLE 4

Oral estrogen treatment:
$IGF_1$ (= somatomedin C) as an expression of hypophyseal secretion of growth hormones according to R. Krattenmacher et al. (J. Steroid. Biochem. Molec. Biol.; 48 (23), pp. 207–214 (1994))

| Substances | Dosage (100 μg/animal/day p.o. d1–d7) | | |
|---|---|---|---|
| Experiment A | d 0 | d 4 | d 8 |
| Control | 825.7 ± 56.5 | 811.4 ± 77.3 | 774.8 ± 82.5 |
| E2 | 717.4 ± 80.8 | 623.6 ± 100.0 | 601.1 ± 108.8 |
| EE | 704.6 ± 70.4 | 547.0 ± 88.7 | 393.6 ± 71.1 |
| J 271 | 826.4 ± 96.7 | 593.7 ± 57.0 | 351.5 ± 32.6 |
| J 824 | 733.0 ± 136.6 | 504.3 ± 131.8 | 341.4 ± 100.0 |

Angiotensin I (AI) (see Tables 5a and 5b) AI values at various doses (1.0 or 10.0 or 100.0 μg/animal/day, selected substances):

At the lowest dose, increased AI values are only observed under the influence of J 824. Estradiol had no recognizable effect at any dose throughout the experiment. EE and J 824 result in sharp increases of AI that can be detected as early as on day 4 of treatment at doses of 10 or 100 μg. J 271 had no clear effect on AI at a dose of 10 μg/day. At a dose of 100 μg/day there are increases in AI values but these are significantly lower than those observed under the influence of EE or J 824 at a similar dose.

TABLE 5a

Effects of oral estrogen treatment on hepatic parameters
Angiotensin I: Dose-action relationship on day 4

| Substances Experiment A | Dosage (μg/animal/day p.o. d1–d7) | | | |
|---|---|---|---|---|
| | 0.1 | 1 | 10 | 100 |
| Control | 426.4 ± 20.6 | 424.9 ± 33.1 | 403.6 ± 24.4 | 406.1 ± 65.4 |
| E2 | 376.2 ± 48.3 | 359.8 ± 53.4 | 412.8 ± 66.6 | 497.7 ± 69.0 |
| EE | 408.2 ± 31.2 | 402.2 ± 30.3 | 572.2 ± 35.0 | 930.1 ± 146.2 |
| J 271 | 380.8 ± 35.8 | 383.8 ± 47.1 | 435.2 ± 53.8 | 734.0 ± 75.7 |
| J 824 | 434.3 ± 65.5 | 355.2 ± 29.5 | 658.9 ± 18.8 | 1029.7 ± 174.7 |

TABLE 5b

Effects of oral estrogen treatment on hepatic parameters
Angiotensin I: Dose-action relationship on day 8

| Substances Experiment A | Dosage (μg/animal/day p.o. d1–d7) | | | |
|---|---|---|---|---|
| | 0.1 | 1 | 10 | 100 |
| Control | 436.2 ± 11.9 | 447.1 ± 30.0 | 346.6 ± 50.5 | 353.1 ± 42.1 |
| E2 | 449.5 ± 55.1 | 392.9 ± 32.0 | 335.5 ± 24.9 | 464.3 ± 16.7 |
| EE | 473.7 ± 19.7 | 492.6 ± 29.1 | 498.7 ± 26.1 | 833.1 ± 137.2 |
| J 271 | 462.2 ± 71.3 | 425.9 ± 43.9 | 373.4 ± 42.3 | 668.2 ± 68.6 |
| J 824 | 482.2 ± 39.8 | 606.7 ± 188.2 | 655.0 ± 64.7 | 958.3 ± 207.6 |

TABLE 6a

Effects of oral estrogen treatment on hepatic parameters
Total cholesterol levels (mg/dl, mean value ± standard deviation):
Dose-action relationship on day 4

| Substances Experiment A | Dosage (μg/animal/day p.o. d1–d7) | | | |
|---|---|---|---|---|
| | 0.1 | 1 | 10 | 100 |
| Control | 113.4 ± 21.8 | 113.7 ± 12.5 | 94.9 ± 12.6 | 85.2 ± 13.3 |
| E2 | 91.4 ± 10.6 | 94.2 ± 16.8 | 94.9 ± 10.2 | 74.3 ± 10.7 |
| EE | 81.0 ± 3.3 | 82.4 ± 15.8 | 30.3 ± 9.6 | 6.8 ± 3.2 |
| J 271 | 96.0 ± 15.0 | 108.5 ± 10.3 | 92.4 ± 12.1 | 24.5 ± 14.4 |
| J 824 | 94.2 ± 14.6 | 68.5 ± 7.1 | 16.6 ± 2.8 | 6.9 ± 7.5 |

TABLE 6b

Effects of oral estrogen treatment on hepatic parameters
Total cholesterol levels (mg/dl, mean value ± standard deviation):
Dose-action relationship on day 8

| Substances Experiment A | Dosage (μg/animal/day p.o. d1–d7) | | | |
|---|---|---|---|---|
| | 0.1 | 1 | 10 | 100 |
| Control | 111.7 ± 20.9 | 113.6 ± 17.7 | 93.0 ± 13.2 | 93.4 ± 10.3 |
| E2 | 92.7 ± 7.6 | 88.8 ± 7.5 | 98.5 ± 5.9 | 68.4 ± 12.7 |
| EE | 86.5 ± 9.6 | 80.2 ± 14.4 | 39.8 ± 10.2 | 5.5 ± 3.3 |
| J 271 | 91.1 ± 18.3 | 101.4 ± 6.3 | 81.9 ± 12.6 | 18.6 ± 8.3 |
| J 824 | 92.3 ± 12.6 | 70.0 ± 9.0 | 18.1 ± 3.3 | 8.4 ± 10.7 |

TABLE 7a

Effects of oral estrogen treatment on hepatic parameters
HDL cholesterol levels (mg/dl, mean value ± standard deviation):
Dose-action relationship on day 4

| Substances Experiment A | Dosage (μg/animal/day p.o. d1–d7) | | | |
|---|---|---|---|---|
| | 0.1 | 1 | 10 | 100 |
| Control | 61.7 ± 5.7 | 58.4 ± 7.0 | 60.5 ± 11.3 | 51.2 ± 4.9 |
| E2 | 49.1 ± 7.8 | 50.9 ± 6.1 | 55.0 ± 6.9 | 43.7 ± 7.6 |
| EE | 49.6 ± 2.9 | 47.1 ± 8.5 | 19.5 ± 8.4 | 3.6 ± 1.3 |
| J 271 | 57.6 ± 6.5 | 57.1 ± 7.1 | 54.6 ± 5.7 | 13.2 ± 14.0 |
| J 824 | 52.5 ± 7.4 | 40.3 ± 8.0 | 7.1 ± 2.0 | 4.7 ± 5.4 |

TABLE 7b

Effects of oral estrogen treatment on hepatic parameters
HDL cholesterol levels (mg/dl, mean value ± standard deviation):
Dose-action relationship on day 8

| Substances Experiment A | Dosage (μg/animal/day p.o. d1–d7) | | | |
|---|---|---|---|---|
| | 0.1 | 1 | 10 | 100 |
| Control | 62.9 ± 13.2 | 60.2 ± 2.5 | 55.9 ± 10.2 | 58.8 ± 10.9 |
| E2 | 51.0 ± 4.6 | 52.3 ± 4.1 | 51.5 ± 3.9 | 46.0 ± 9.2 |
| EE | 52.2 ± 4.1 | 49.5 ± 6.9 | 26.5 ± 7.8 | 2.4 ± 0.9 |
| J 271 | 57.3 ± 6.0 | 59.6 ± 6.8 | 49.9 ± 6.0 | 10.7 ± 8.2 |
| J 824 | 55.3 ± 8.8 | 48.2 ± 6.1 | 7.2 ± 2.4 | 5.0 ± 7.9 |

Dose-action relationships on days 4 and 8 for angiotensin I, total cholesterol and HDL cholesterol (cf. Tables 5a, 5b, 6a, 6b, 7a, and 7b):

Angiotensin I (cf. Tables 5a and 5b):

Estradiol at best has marginal stimulating influence on the angiotensin I level. Values for of the compound according to Example 2 were clearly below those for EE.

Total cholesterol levels (cf. Tables 6a and 6b), and HDL cholesterol levels (cf. Tables 7a and 7b):

In the rat, estrogens reduce cholesterol levels in the blood to a very great extent depending on dosage. Trends observed show the same tendency for HDL and total cholesterol levels. Doses of 10 to 100 $\mu$g result in very low cholesterol concentrations in the blood for most of the substances tested. Several substances cause marked changes already at a dose of 1 $\mu$g/animal. Only estradiol (all doses) and the compound according to Example 2 (up to 10 $\mu$g) did not reduce cholesterol levels in the blood. Even if the highest dose of the compound according to Example 2 is applied, the drop in total and HDL cholesterol levels in the blood is still recognizably lower than that caused by EE.

The following Examples shall explain the present invention:

EXAMPLE 1

General instructions for preparing 3-amidosulfonyloxy derivatives of estra-1,3,5(10)-derivatives The estra-1,3,5(10)-derivative to be esterified, amidosulfonyl chlorid, alkali or alkaline-earth hydroxide, and quaternary salt as phase transition catalyst are added to a mixture of a suitable solvent and water while stirring heavily.

The batch is kept agitated until analytical proof (using thin-layer chromatography) is obtained that esterification is completed. Optionally, it may be useful to work at temperatures between 50° C. and 100° C. to reduce reaction times. Afterwards, the two phases are separated. The aqueous phase is re-extracted, and the combined organic phases are washed, in the following order, in dilute hydrochloric acid, saturated sodium hydrogencarbonate solution, and water. The extract is then dried over anhydrous sodium sulfate and evaporated to dryness under reduced pressure. The residue is recrystallized from a proper solvent.

EXAMPLE 2 (=J 271)

Preparation of 17β-hydroxy-19-nor-17α-pregna-1,3,5(10)-triene-20-in-3-yl N,N-diethyl-sulfamate 1 g of 17α-ethinyl estradiol, 0.4 g of sodium hydroxide, 0.08 g of benzyl triethyl ammonium chloride, and 1.16 g of N,N-diethyl-amidosulfonyl-chloride are reacted as described in Example 1 in a mixture of 5 ml of dichloromethane and 2.5 ml of water.

The title compound is obtained after work-up and recrystallizing the crude product from diisopropyl ether.

Fp.: 113–115° C.; [α]D: +3° C. (chloroform, c=1)

EXAMPLE 3 (=J 272)

Preparation of 17β-hydroxy-19-nor-17α-pregna-1,3,5(10)-trien-20-in-3-yl N,N-pyrrolidinosulfonate 1 g of 17α-ethinyl estradiol, 0.57 g of potassium hydroxide, 0.08 g of benzyl triethyl ammonium chloride, and 1.15 g of pyrrolidinosulfonyl chloride are reacted as described in Example 1 in a mixture of 5 ml of dichloromethane and 2.5 ml of water.

The title compound is obtained after work-up and recrystallizing the crude product from diisopropyl ether.

Fp.: 121–122° C.; [α]D: +10° C. (chloroform, c=1)

EXAMPLE 4 (=J 981)

Preparation of 17β-hydroxy-estra-1,3,5(10)-trien-3-yl N, N-diethyl-sulfamate 0.92 g of estradiol, 0.4 g of sodium hydroxide, 0.08 g of benzyl triethyl ammonium chloride, and 1.16 g of N,N-diethyl-amidosulfonyl chloride are reacted as described in Example 1 in a mixture of 5 ml of dichloromethane and 2.5 ml of water.

The title compound is obtained after work-up and recrystallizing the crude product from methanol.

Fp.: 175–176° C.; [α]D: +57° C. (chloroform, c=1)

EXAMPLE 5 (=J 983)

Preparation of 17β-hydroxy-14α,15α-methylen-estra-1,3,5(10)-trien-3-yl N,N-diethyl-sulfamate 2 g of 14α,15α-methylen-estra-1,3,5(10)-triene-3, 17β-diol are suspended with 30 ml of toluene, 4 ml of water, 0.32 g of benzyl triethyl ammonium chloride, 2.94 g of N,N-diethyl-amidosulfonyl chloride and 2.1 ml of 40% aqueous sodium hydroxide solution and heated while stirring for two hours to an internal temperature of 80° C.

After allowing the batch to cool down to room temperature, it is worked-up as described in Example 1. The crude product obtained is chromatographed on silica gel (particle sizes 0.063 to 0.2 mm). The title compound is obtained after elution using chloroform/ethyl acetate and recrystallizing from methanol.

Fp.: 68–73° C.; [α]D: +98° C. (chloroform, c=1)

EXAMPLE 6 (=J 989)

Preparation of 16α,17β-dihydroxy-estra-1,3,5(10)-trien-3-yl N,N-dimethyl-sulfamate 120 ml of water, 1.58 g of benzyl triethyl ammonium chloride, 7.44 ml of N,N-dimethyl-amidosulfonyl chloride and 4 ml of 40% aqueous sodium hydroxide solution are mixed under stirring with a solution of 2 g estriol in 800 ml of toluene at a temperature of 80° C. The batch is heated to 80° C. The reaction solution is kept at a pH value of 10 during this time by adding 40% aqueous sodium hydroxide solution. The batch is allowed to cool down to room temperature when the parent compounds have been reacted completely, and worked-up as described in Example 1. The residue obtained is recrystallized from acetone/n-hexane and yield the title compound.

Fp.: 180–181° C.; [α]D: +48° C. (chloroform, c=1)

EXAMPLE 7 (=J 804)

Preparation of Estra-1,3,5(10)-trien-17-on-3-yl N, N-diethyl-sulfamate 0.91 g of estrone, 1.73 g of barium hydroxide, 0.089 g of cyclohexyl triethyl ammonium chloride, and 1.16 g of N,N-diethyl-amidosulfonyl-chloride are reacted as described in Example 1 in a mixture of 5 ml of tertiary amyl alcohol and 2.5 ml of water.

The title compound is obtained after work-up and recrystallizing the crude product from methanol.

Fp.: 176–180° C.; [α]D: +109° C. (chloroform, c=1)

EXAMPLE 8 (=J 665)

Preparation of 17β-hydroxy-19-nor-17α-pregna-1,3,5(10)-trien-20-in-3-yl N,N-dimethyl-sulfamate 1 g of 17α-ethinyl estradiol, 2.4 g of sodium hydroxide, 0.24 g of triethyl benzyl ammonium chloride, and 3.6 ml of N,N-dimethyl-amidosulfonyl-chloride are reacted as described in Example 1 in a mixture of 30 ml of dichloromethane and 6.6 ml of water.

The title compound is obtained after work-up, chromatographic purification, and recrystallizing of the reaction product from acetone/n-hexane.

Fp.: 157–160° C.; [α]D: +4° C. (chloroform, c=1)

EXAMPLE 9 (=J 982)

Preparation of 17β-hydroxy-14α,15α-methylen-estra-1,3,5(10)-trien-3-yl N,N-dimethyl-sulfamate 1 g of 14α,15α-methylene-estra-1,3,5(10)-trien-3,17β-diol, 2.4 g of sodium hydroxide, 0.24 g of triethyl benzyl ammonium chloride, and 3.6 ml of N,N-dimethyl-amidosulfonyl-chloride are reacted as described in Example 1 in a mixture of 30 ml of dichloromethane and 6.6 ml of water.

The title compound is obtained after work-up, chromatographic purification, and recrystallizing of the reaction product from acetone.

Fp.: 193–196° C.; [α]D: +108° C. (chloroform, c=1)

EXAMPLE 10 (=J 984)

Preparation of 16α,17β-dihydroxy-estra-1,3,5(10)-trien-3-yl N,N-diethyl-sulfamate 2 g of estriol, 5.2 g of sodium hydroxide, 1.72 g of triethyl benzyl ammonium chloride and 9.75 ml of N,N-diethyl-amidosulfonyl chloride are reacted as described in Example 1 in a mixture of 800 ml of toluene and 128 ml of water. The title compound is obtained after reprocessing, chromatographic purification, and recrystallizing from acetone.

Fp.: 121–124° C.; [α]D: +44° C. (chloroform, c=1)

What is claimed is:

1. A method of treating a patient, comprising the steps of:
providing a pharmaceutical preparation to a patient requiring reduced estrogenic effects in their liver, the pharmaceutical preparation containing estra-1,3,5(10)-triene derivatives as active ingredients of the general formula I

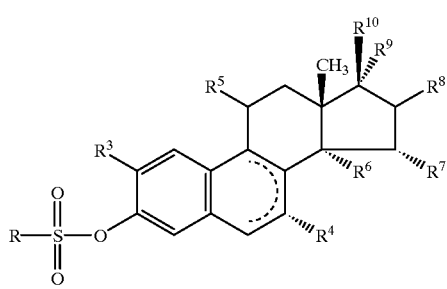

I wherein

R is an $R^1R^2N$ group, $R^1$ and $R^2$ are independent of each other and represent a hydrogen atom or a $C_1$–$C_5$ alkyl radical, $R^3$ is a hydrogen atom, a hydroxy group, or an alkoxy group containing 1 to 5 C atoms, $R^4$ is a hydrogen atom or a $C_1$–$C_5$ alkyl radical, $R^5$ is a hydrogen atom, a hydroxy group, an esterified hydroxy group, a haloalkyl or alkoxy group containing 1 to 5 C atoms, $R^6$ and $R^7$ are hydrogen atoms, or together form a methylene group, $R^8$, $R^9$ and $R^{10}$ are independent of each other and represent a hydrogen atom or a hydroxy group, with ring B optionally containing one or two double bonds or, optionally, $R^9$ being an alkynyl radical containing between 3 and 5 carbon atoms, or $R^6$ and $R^9$ representing a vinylene or ethylene group; and using the prepared pharmaceutical preparations for at least one of (a) contraception, (b) treatment of prostatic carcinomas, and (c) hormone replacement therapy, said pharmaceutical preparations having reduced estrogenic effects in the liver of a patient in which they are being used as compared to natural and synthetic estrogens.

2. The method of claim 1, wherein the step of using the pharmaceutical preparations comprises the steps of:
forming the prepared pharmaceutical preparations into at least one of tablets, tablets having controlled release, lozenges, pills, capsules, film tablets, and film tablets having controlled release; and
orally administering the formed pharmaceutical preparations to the patient.

3. The method of claim 1, wherein the pharmaceutical preparations contain at least one of the following:
17β-hydroxy-estra-1,3,5(10),7-tetraen-3-yl N,N-diethyl-sulfamate,
17β-hydroxy-estra-1,3,5(10),6,8-pentaen-3-yl N,N-dimethyl-sulfamate,
17βhydroxy-14α,15α-methylen-estra-1,3,5(10)-trien-3-yl N,N-dimethyl-sulfamate,
17β-hydroxy-14α,15α-methylen-estra-1,3,5(10)-trien-3-yl N,N-diethyl-sulfamate,
17β-hydroxy-14α,15α-methylen-estra-1,3,5(10)-trien-3-yl N-methyl-sulfamate,
17β-hydroxy-14α,15α-methylen-estra-1,3,5(10)-trien-3-yl sulfamate,
17β-hydroxy-14α,15α-methylen-estra-1,3,5(10),7-tetraen-3-yl N,N-di-methyl-sulfarnate,
17β-hydroxy-14α,15α-methylen-estra-1,3,5(10), 6,8-pentaen-3-yl N,N-diethyl-sulfamate,
17β-hydroxy-14α,15α-methylen-estra-1,3,5 (10), 8-tetraen-3-yl N,N-dimethyl-sulfamate,
11β-chloromethyl-17β-hydroxy-estra-1,3,5(10)-trien-3-yl N,N-dimethyl sulfamate, and
16α,17β-dihydroxy-14α,17α-ethylen-estra- 1,3,5(10)-trien-3-yl N,N-diethyl-suilirate.

4. A method of treating a patient, comprising the steps of:
providing a pharmaeutical preparation to a patient requiring reduced estrogenic effects in their liver, the pharmaceutical preparation containing estra-1,3,5(10)-trience derivatives as active ingredients selected from the group consisting of
17β-hydroxy-14α,15α-methylen-estra-1,3,5(10)-trien-3-yl pyrrolidinosulfonate,
17β-hydroxy-14α,15α-methylen-estra-1,3,5(10)-trien-3-yl morpholinosulfonate, 14α,17α-ethylene-17βhydroxy-estra-1,3,5(10)-trien-3-yl pyrrolidinosulfonate, and
17β-hydroxy-7α-methyl-estra-1,3,5(10)-triene-3,11β-diyl 3-N,N-dimethyl-sulfamate-11-nitrate,
using the prepared pharmaceutical preparations for at least one of (a) contraception, (b) treatment of prostatic carcinomas, and (c) hormone replacement therapy, said pharmaceutical preparations having reduced estrogenic effects in the liver of a patient in which they are being used as compared to natural and synthetic estrogens.

* * * * *